United States Patent [19]
Stern

[11] Patent Number: 6,138,689
[45] Date of Patent: Oct. 31, 2000

[54] TOOTHBRUSH

[76] Inventor: Mina Miri Stern, 6 Uziel St., Tel Aviv, Israel, 59463

[21] Appl. No.: 09/355,716
[22] PCT Filed: Feb. 3, 1998
[86] PCT No.: PCT/IL98/00051
   § 371 Date: Aug. 3, 1999
   § 102(e) Date: Aug. 3, 1999
[87] PCT Pub. No.: WO98/36661
   PCT Pub. Date: Aug. 27, 1998

[30] Foreign Application Priority Data

Feb. 19, 1997 [IL] Israel .................................. 120255
Jan. 25, 1998 [IL] Israel .................................. 123043

[51] Int. Cl.$^7$ ........................... A45D 44/18; A46B 11/00
[52] U.S. Cl. ...................... 132/309; 15/167.2; 132/311; 132/328
[58] Field of Search ................. 132/308, 309, 132/311, 323, 324, 325, 326, 327, 328; 15/167.2

[56] References Cited

U.S. PATENT DOCUMENTS

| | | | |
|---|---|---|---|
| 715,263 | 12/1902 | Haussmann | 15/167.2 |
| 1,353,780 | 9/1920 | Mueller | 15/167.2 |
| 1,389,624 | 9/1921 | Carroll | 15/167.2 |
| 1,519,515 | 12/1924 | Stonehill . | |
| 1,599,339 | 9/1926 | Loyd | 15/167.2 |
| 1,709,262 | 4/1929 | Henderhan | 15/167.2 |
| 1,868,368 | 7/1932 | Reese | 15/167.2 |
| 2,528,992 | 11/1950 | Barr | 15/167.2 |
| 2,743,833 | 7/1956 | Vecchio | 132/309 |
| 3,934,298 | 1/1976 | Kim . | |
| 5,088,145 | 2/1992 | Whitefiled | 15/167.2 |
| 5,228,466 | 7/1993 | Klinkhammer | 132/309 |
| 5,316,027 | 5/1994 | Klinkhammer | 132/309 |
| 5,331,983 | 7/1994 | Father | 132/309 |
| 5,351,358 | 10/1994 | Larrimore . | |
| 5,360,026 | 11/1994 | Klinkhammer | 132/309 |
| 5,497,526 | 3/1996 | Klinkhammer . | |
| 5,622,195 | 4/1997 | Lee | 132/311 |
| 5,647,385 | 7/1997 | Zebhur . | |
| 5,758,380 | 6/1998 | Vrignaud | 15/167.2 |
| 5,769,102 | 6/1998 | Zebuhr | 15/167.2 |
| 5,934,762 | 8/1999 | Vrignaud | 15/167.2 |

FOREIGN PATENT DOCUMENTS 44 02 366   6/1994   Germany .

*Primary Examiner*—Todd E. Manahan
*Attorney, Agent, or Firm*—Shalom Wertsberger; Saltamar Innovations

[57] ABSTRACT

A toothbrush having at least one brushing head disposed at one of its ends, the toothbrush comprising a handle, the handle comprising a longitudinal grip portion and at least one bifurcated end portion. The bifurcated end portion is having two cleansing means carrying members extending in parallel directions, the carrying members being sufficiently spaced so as to allow mounting cleansing means thereon. The cleansing means comprise at least one of the following: (i) a pair of brushing heads comprising bristle bundles arranged at the extremities of the carrying members; (ii) a dental floss a length of which is tautly stretched across the carrying members. The toothbrush further having a lateral sheath having two open ended sides, in which the handle of an oral hygiene implement is removably sheathed.

36 Claims, 5 Drawing Sheets

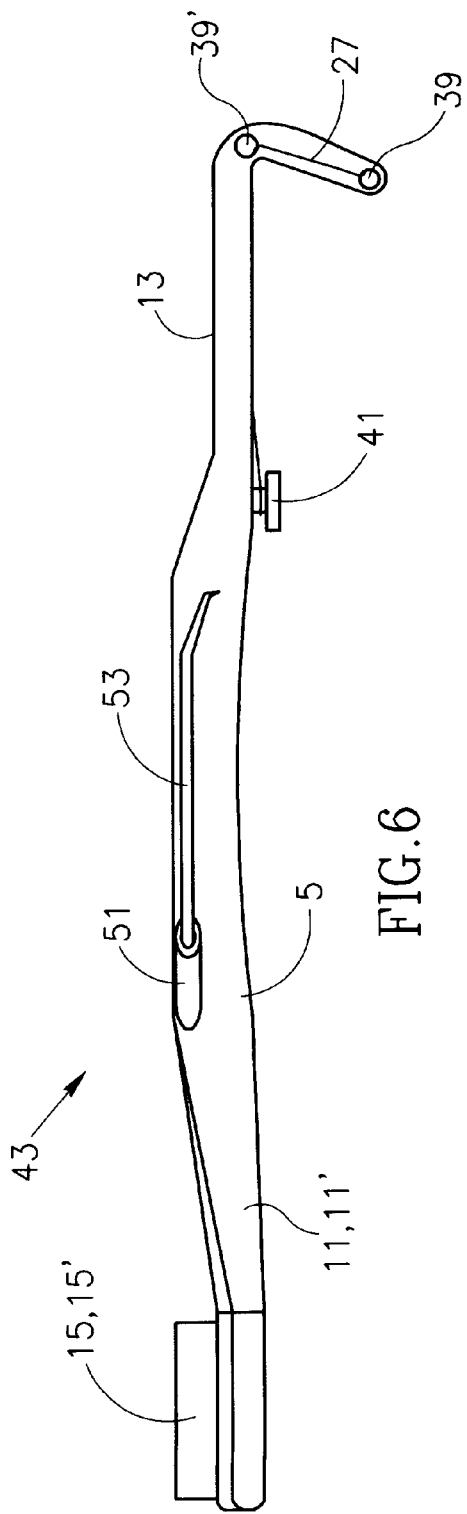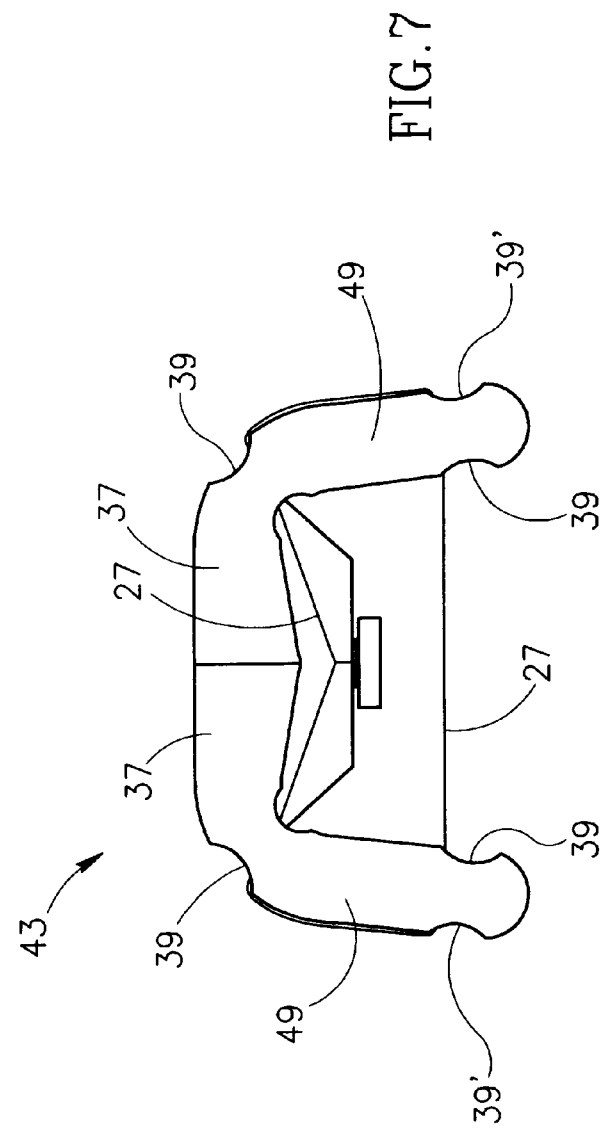

TOOTHBRUSH

TECHNICAL FIELD

The present invention concerns toothbrushes in general, and toothbrushes combined with plaque removers, dental floss or toothpicks in particular.

BACKGROUND ART

Toothbrushes and other tooth cleaning aids, namely—plaque removers, toothpicks and dental floss are considered essential for effective cleaning of the teeth and gum surfaces and for general mouth hygiene. As such, they are highly recommended for frequent use—at least on a daily basis and preferably twice or three times a day. However, the effective cleaning of the teeth and gum surfaces requires complicated procedures, exact maneuvers by the human arm and it is time consuming. Moreover, since most people brush and clean their teeth early in the morning or late in the evening just prior to retiring, it is beyond the tolerance of most of them to brush their teeth properly, not to mention the use of a plaque remover, a toothpick or a dental floss that is often entirely neglected. In addition, since most conventional toothbrushes do not adapt to easy brushing, the users often resort to simple brushing without performing the well known effective brushing technique. Such technique requires back and forth strokes while the toothbrush head is held at approximately 45° angle, with the bristles brushing the teeth surfaces and the gap between the teeth and the gums (Sulcus). Furthermore, the toothbrush is almost always available for use, considering the awareness of individuals to its importance. However, due to the lack of awareness of the significance of the routine use of plaque removers, dental floss, and toothpicks,—these tools are often absent, stored, or out of immediate reach, and therefore their use is often overlooked.

It is therefore, an object of this invention, to provide a novel toothbrush that ameliorates effective brushing of all surfaces of the teeth without requiring grossly complicated maneuvers by the user, and also aid in controlling tooth caries and other tooth diseases.

Another object of this invention is to provide a novel toothbrush that in addition, combines dental floss for flossing of interproximal areas, or a toothpick, or an auxiliary subgingival brushing bristle bundles or any combination thereof.

A further object of this invention is to provide a novel toothbrush that provides subgingival brush heads or bristles that can easily enter and clean the sulcus, or sulcular pocket—which is the tooth surface hidden behind the gum tissue or below the gum line of the user, contact a tooth surface below the gumline to remove bacteria adhering to the tooth surface and aid in preventing or controlling various periodontal diseases.

Still, another object of this invention is to provide a novel toothbrush that maintains a controllable gap between a pair of adjacent arms holding brushheads or floss, therefore allowing control of head pressure.

Yet, a further object of this invention is to provide a novel toothbrush that allows for removable installation of auxiliary cleaning tools such as toothbrushes, gum brushes, brushes intended for aid in plaque removal, dental floss, toothpicks, or any combination thereof, all of which may be optionally replaceable or disposable.

Still, a further object of this invention is to provide a multipurpose toothbrush, synergically combining several functions in one portable device that comprises a comprehensive oral hygiene system with elements that may be replaceable or interchangeable, in order to meet oral hygiene needs.

These and other objectives are provided by the invention to be described below.

DISCLOSURE OF INVENTION

There is thus provided according to the present invention a novel toothbrush having at least one brushing head disposed at one end, the toothbrush includes a handle, the handle having a longitudinal grip portion and at least one bifurcated end portion. The bifurcated end portion has two cleansing means carrying members extending in parallel directions, the carrying members are spaced suffficiently, in order to allow mounting of cleansing means thereon, while the cleansing means include at least one of the following: (i) a pair of brushing heads having bristle bundles arranged at the extremities of the carrying members; (ii) a dental floss strand a length of which is tautly stretched across the carrying members.

Optionally, the pair of brushing heads may include two brushing heads holding bristle arrangements inclined to each other, the pair of brushing heads being connected to the handle by means of the curved neck portions of the carrying members. Furthermore, the free ends of bristles of the brushing heads converge at an angle. The angle between the heads preferably ranges between 60° and 120° and most preferably is at about 90°.

Preferably, the pair of carrying members includes flexible neck portions allowing the user to temporarily bring the carrying members closer together, in a resilient manner, by applying finger pressure thereto.

Further optionally, the pair of brushing heads includes two oppositely facing small brushing heads holding small bristle arrangements for simultaneously brushing both sides of a tooth, the pair of brushing heads being connected to the handle by means of the curved neck portions of the carrying members. The oppositely facing small brushing heads may be spaced so as to match the typical width of a tooth. The small brushing heads may also be inclined to one another at an angle ranging between 160° and 180°, and preferably close to 170°. Further preferably, the small brushing heads are connected to the carrying members by proper connection means allowing removal and discarding of the small brushing heads.

Optionally, the longitudinal grip portion includes a protrusion mounted thereon, around which the dental floss is wrapped and secured, and the carrying members comprise at their tips large openings through which the floss may be passed and tautly stretched.

In a preferred embodiment, the carrying members include two types of the cleansing means spaced apart one above the other so that a first type of the cleansing means is disposed at the upper extremities of the carrying members and a second type of the cleansing means is disposed at the lower extremities of the carrying members, respectively. Preferably, the cleansing means carrying members each include a head portion connected to the handle by a neck portion. The head portions include a leg curving downward from the neck portion. One type of the cleansing means is disposed at the lower extremities of both legs and another type of the cleansing means is disposed in proximity to the connection point of the neck portions and the head portions, respectively. The first type of cleansing means includes the dental floss, and the second type of cleansing means includes the two facing small brushing heads.

This invention also features a toothbrush that includes a lateral sheath in which an oral hygiene implement, such as a toothpick, may be removably sheathed.

Further optionally, the longitudinal grip portion includes a battery powered electric motor to impart vibrating motion or motions of tufts of the bristle bundles.

Further features and advantages of the invention will be apparent from the description below, given by way of example only.

BRIEF DESCRIPTION OF THE DRAWINGS

The present invention will be further understood and appreciated from the following detailed description, taken in conjunction with the following enclosed drawings in which like numerals designate correspondingly analogous elements or sections throughout, and in which:

FIG. 6 is a perspective side view of another embodiment constructed and operative in accordance with the invention;

FIG. 7 is a partial rear view of the embodiment of FIG. 6;

BEST MODES FOR CARRYING OUT THE INVENTION

Figure 1A:
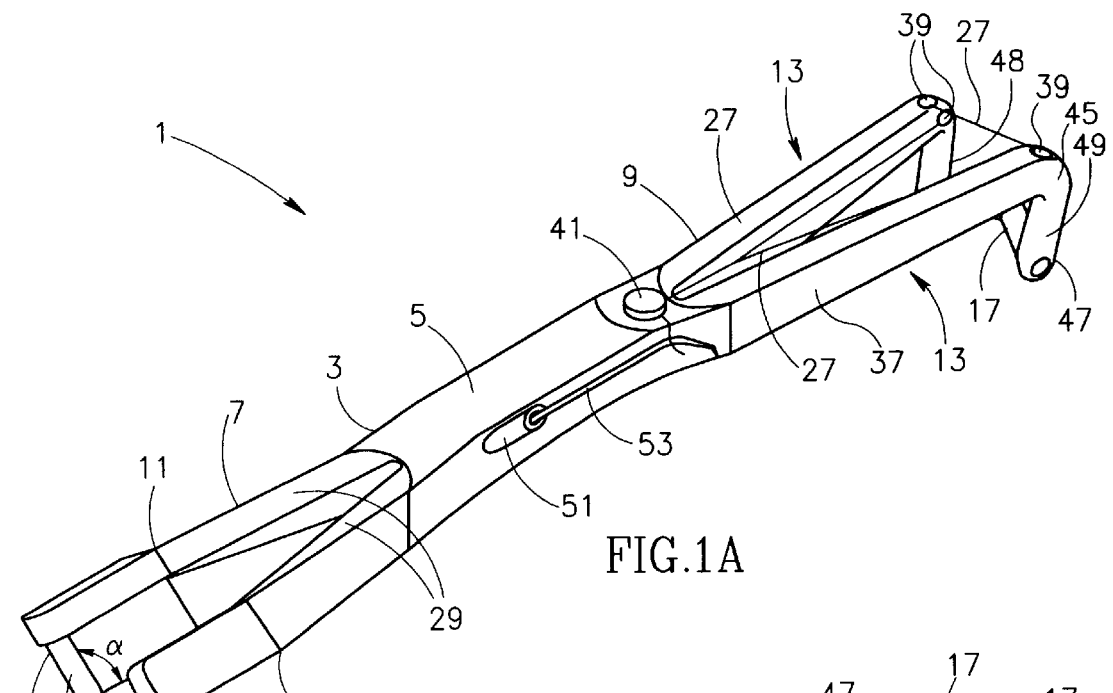
FIG. 1A is a perspective upper view of one embodiment constructed and operative in accordance with the invention.
Figure 1B:
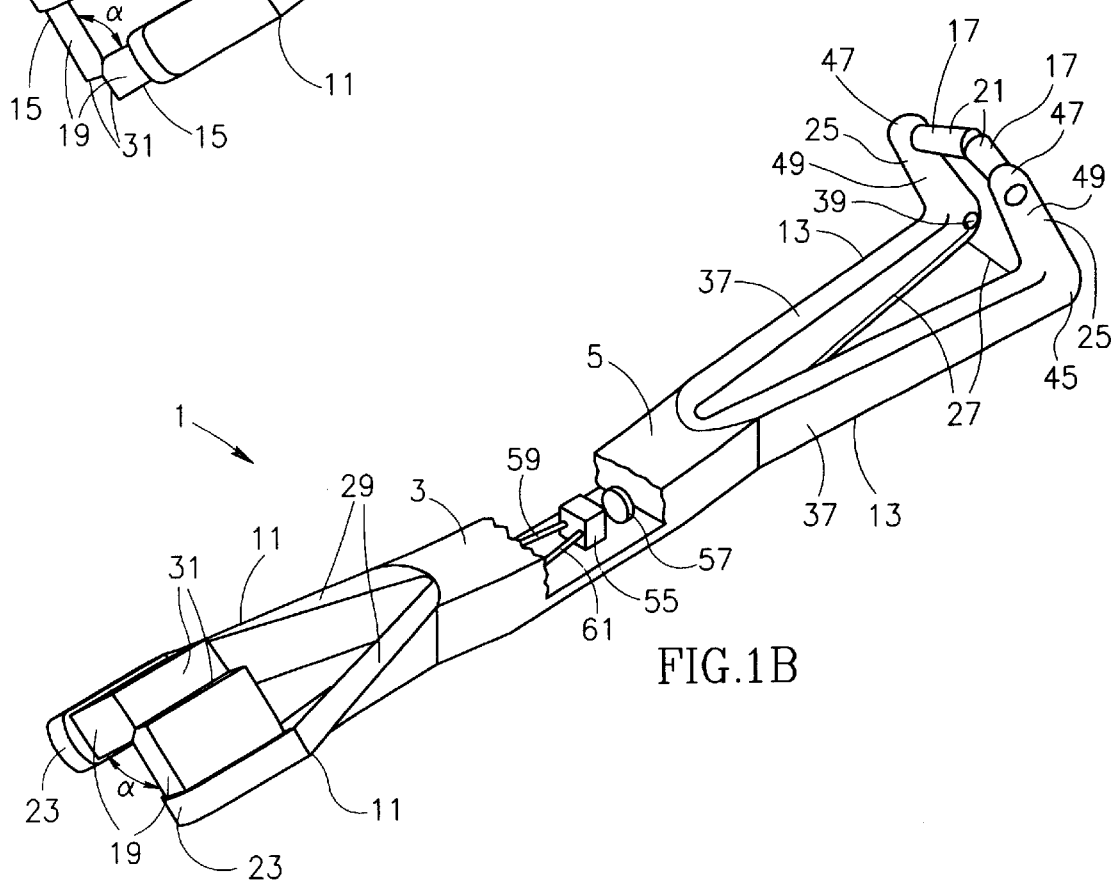
FIG. 1B is a perspective lower view of the embodiment of FIG. 1.
Figure 2:
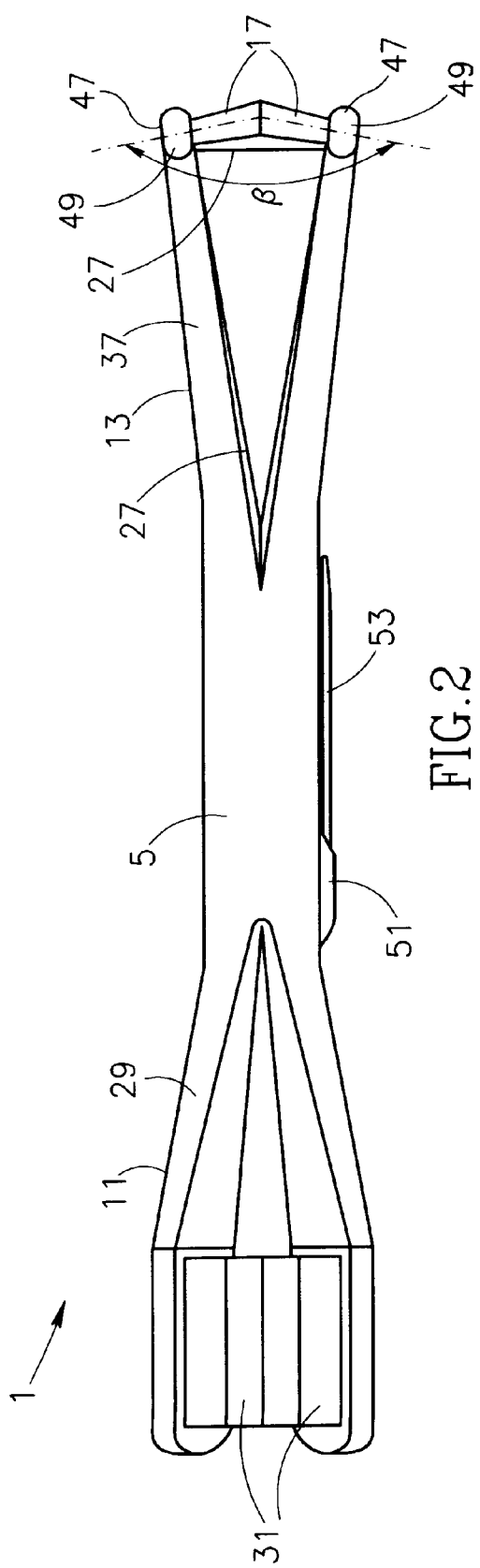
FIG. 2 is a bottom view of the embodiment of FIG. 1.
Figure 3:
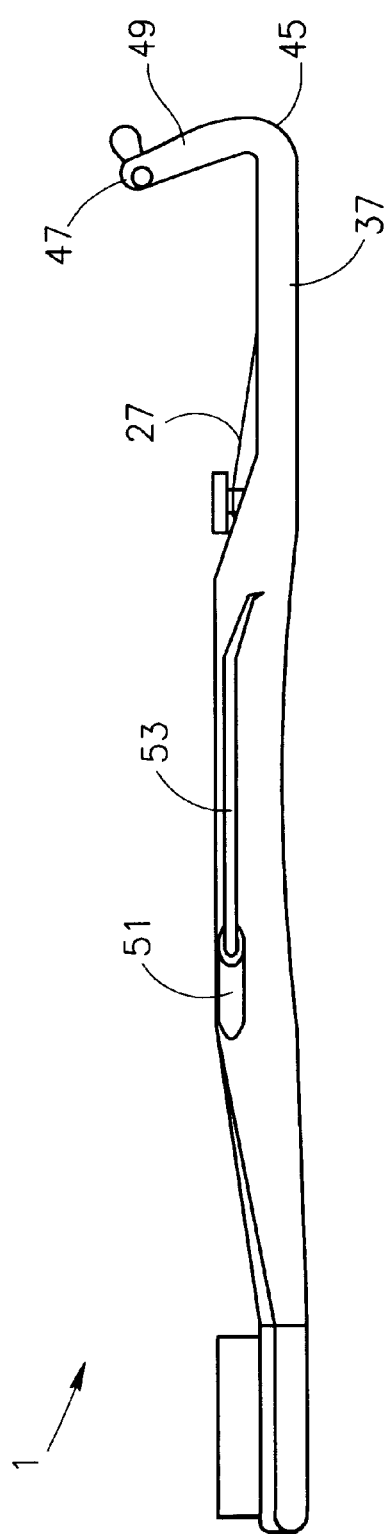
FIG. 3 is a side view of the embodiment of FIG. 1.
Figure 4:
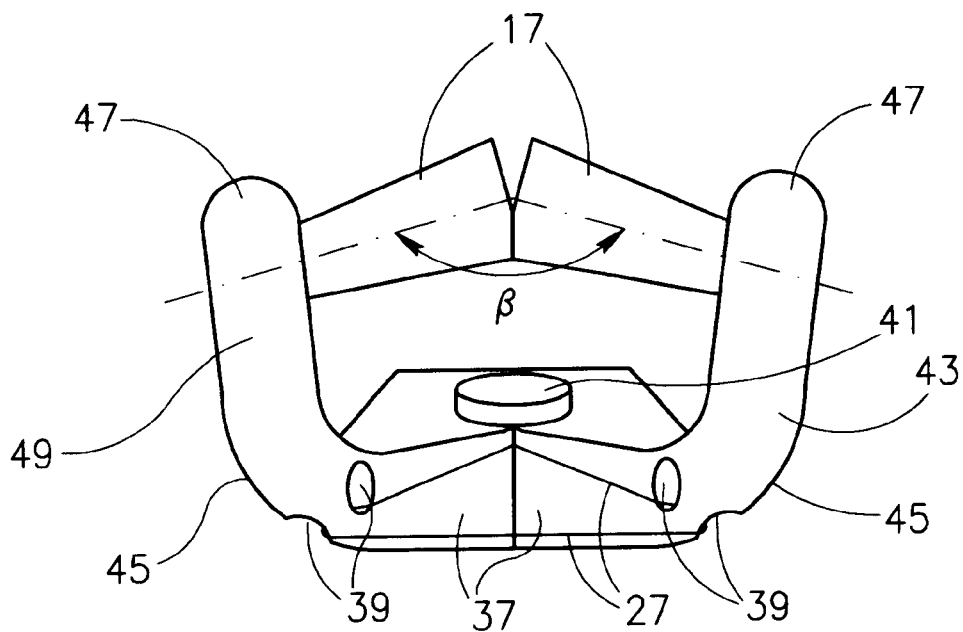
FIG. 4 is a partial rear view of the embodiment of FIG. 1.

In reference to FIGS. 1 to 5, there is shown a toothbrush 1 comprising in combination several optional features of the invention. By definition, toothbrush 1, like any other toothbrush, must have at least one brushing head disposed at one of its ends. Toothbrush 1 comprises a handle 3. Handle 3 comprises a longitudinal grip portion 5 and at least one bifurcated end portion, such as end portions 7 and 9. Bifurcated end portion 7 or 9 has two cleansing means carrying members 11 or 13, respectively, extending in parallel directions. Carrying members 11, 13 are sufficiently spaced so as to allow mounting cleansing means thereon. The cleansing means comprise at least one of the following: (i) a pair of brushing heads 15 or 17, comprising bristle bundles 19 or 21, respectively, arranged in regions 23 or 25, distal to carrying members 11, 13; (ii) a dental floss 27, a length of which is tautly stretched across carrying members 13 respectively. Dental floss 27 may be disposable.

It will be appreciated that a brush head 15 may be configured like a conventional toothbrush and thus it may have any one of the combinations of bristles and shapes for performing routine dental hygiene. Moreover, toothbrush 1 comprises a combined toothbrush having several features assembled together, for the sake of synergetic combination but also for the sake of illustrating various options simultaneously. However, one of the bifurcated end portions may be substituted by a single conventional brush head or entirely eliminated, leaving only one of the novel features as an addition to such conventional toothbrush.

Figure 5:
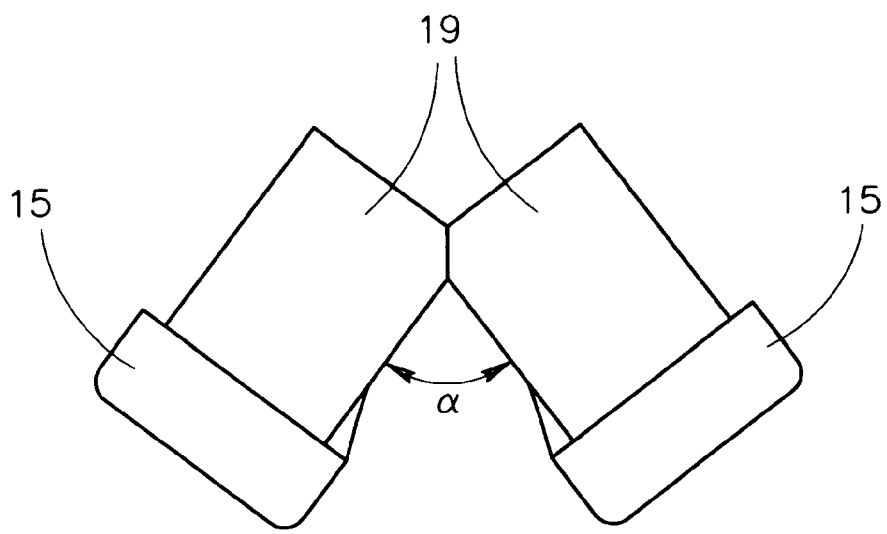
FIG. 5 is a partial front view of the embodiment of FIG. 1.
Figure 8:
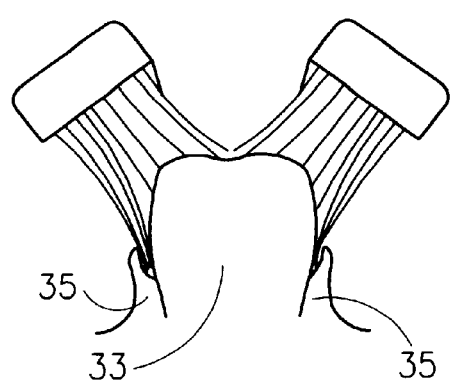
FIG. 8 is a schematic illustration of simultaneous cleaning of two sides of a tooth and their sulcus with one type of a pair of brushing heads constructed and operative in accordance with the invention.
Figure 9:
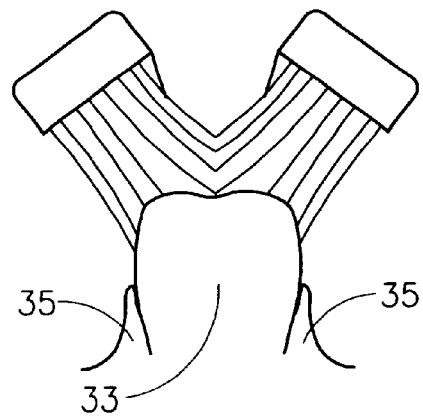
FIG. 9 is a schematic illustration of cleaning the top face of a tooth with the same type of a pair of brushing heads of FIG. 8.
Figure 10:
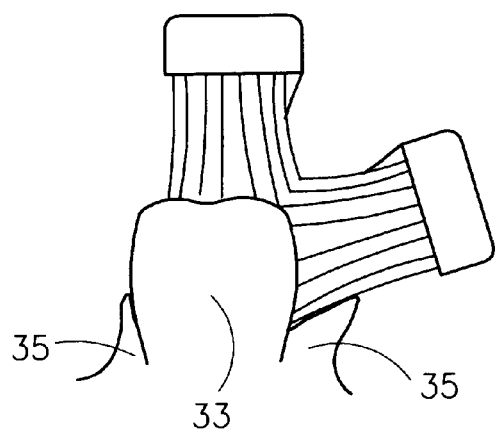
FIG. 10 is a schematic illustration of simultaneous cleaning of one side and top face of a tooth with the same type of a pair of brushing heads of FIG. 8.

Brushing heads 15 comprise two brushing heads holding bristle arrangements 19 inclined to one another at an angle α, best seen in FIG. 5. Brushing heads 15 are connected to handle 5 by means of curved neck portions 29 of carrying members 11. The free ends 31 of the bristles of one brushing head 15 are converged to the free ends 31 of the other brushing head 15 or proximate to such convergence. Angle α preferably ranges between 60° and 120° and most preferably at about 90°. The unique arrangement of brush heads 15 is particularly suitable for simultaneous and effective brushing of both sides of a tooth with optimal back and forth strokes. In this arrangement, each brush head 15 is held at approximately 45° while the bristles touch a tooth 33 and the sulcus between tooth 33 and gums 35, as shown in FIG. 8. Such an advantage is obtained neither at the expense of brushing with different strokes, nor at the expense of effectively reaching various faces of the tooth. FIG. 9 shows the way the top face of a tooth 33 is brushed with the bristles inclined thereto and FIG. 10 illustrates the way top face and one side of a tooth 33 are simultaneously brushed with the bristles configured vertically.

For further control of pressure of brushing heads 15, carrying members 11 preferably comprises flexible neck portions 29, thus allowing the user to resiliently temporarily bring carrying members 11 closer together, in a resilient manner, for example by applying finger pressure. Therefore the user may adjust pressure of the bristles on the teeth and gums and render the brushing action more effective.

Figure 11:
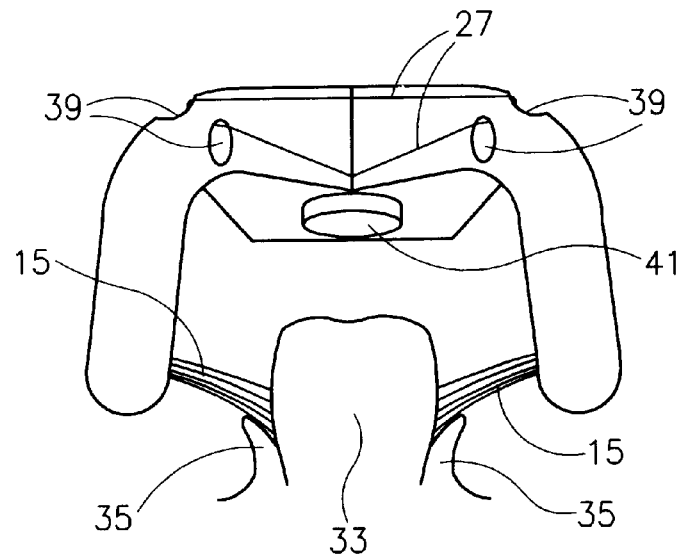
FIG. 11 is a schematic illustration of cleaning two sides of a tooth with another type of a pair of small brushing heads constructed and operative in accordance with the invention.

Referring again to FIGS. 1–5, the pair of brushing heads 17 comprises two oppositely facing small brushing heads 17, holding small bristle arrangements for simultaneously brushing both sides of a tooth, as also seen in FIG. 11. For the present invention, a small brushing head is a head holding small bristle arrangements, of several millimeter across, such as the minor head shown, for example, in FIG. 4 of U.S. Pat. No. 3,934,298. Brushing heads 17 are connected to handle 3 by means of curved neck portions 37 of carrying members 13. Brushing heads 17 may be spaced sufficiently in order to contact both sides of a tooth, to reach interproximal areas between teeth, enhance plaque removal or massaging of the gums or performing any combination of the above tasks. In this context, the distance between the free ends of heads 17 may substantially match the typical width of a tooth. In order to reach more effectively both sides of a tooth, at right angles thereto, brushing heads 17 are preferably slightly inclined to one another at a predetermined angle β, best seen in FIG. 4. Angle β preferably ranges between 160° and 180°, and most preferably at about 170°.

Optionally, brushing heads 17 are removably connected to carrying members 13 by proper connection means as known in the art, allowing removal and discarding of brushing heads 15, to be replaced with new unworn heads. In addition, for further control of the pressure of brushing heads 17, carrying members 13 preferably comprise flexible neck portions 37. This allows the user to temporarily bring carrying members 13 closer together in a resilient manner, e.g., by applying finger pressure for similar purposes as explained for heads 15.

Carrying members 13 may further comprise at their tips large openings 39 through which the dental floss 27 may be passed and tautly stretched. Openings 39 are preferably large enough to permit the user to easily insert and pass floss 27 therethrough. To this end longitudinal grip portion 5 comprises a protrusion 41 mounted thereon, about which floss 27 may be wrapped and secured, allowing the removal and discard of floss 27 and its replacement with fresh floss. Preferably, floss 27 is located close to the upper extremities of carrying members 13, in order to minimize possible entanglement during the use of toothbrush 1.

In an alternate embodiment shown in FIGS. 6 and 7, toothbrush 43 comprises similar grip portion 5 into which brush heads 15 are similarly connected through carrying members 11. Alternately a conventional head 15' may be connected to grip portion 5 with a conventional neck 11'. Brush heads 17 are eliminated, and floss 27 is passed through both openings 39 and 39', so as to retain floss 27 close to the upper extremities of carrying members 13, in order to minimize possible entanglement during the use of toothbrush 43. In fact, the same structure of carrying members 13 may be used for both embodiments of FIGS. 1 and 6. In both embodiments, flexible carrying members 13 allow easy placement of a stretched floss 27 by securing the floss to protrusion 41 while members 13 are pressed together by the fingers of the user. Thus, when the fingers release the pressure, carrying members 13 stretch floss 27 across each other with extra force which is advantageous during the cleaning of interproximal areas between the teeth. Referring again to the embodiment of FIGS. 1–5, it is apparent that carrying members 13 comprise two types of cleansing means spaced one above the other. In this arrangement a first type of the cleansing means—dental floss 27, is disposed at upper extremities 45 of carrying members 13 and a second type of the cleansing means—small brushing heads 17, are disposed at lower extremities 47 of carrying members 13, respectively.

It will be appreciated that the types of cleansing means may be exchanged, replaced or substituted.

In the particular case of the embodiment of FIGS. 1–5, carrying members 13 each comprise a head portion 49 connected to handle 3 by neck portion 37. Head portions 49 comprise a leg curving downward from neck portion 37. In this arrangement one type of the cleansing means (Brushes 17) is disposed at the lower extremities of both of the legs and another type of the cleansing means (floss 27) is disposed at the area 45 of the connection between neck portions 37 and head portion 49, respectively.

Another optional feature of the invention relates to a lateral sheath 51 or sleeve, in which the handle of an oral hygiene implement, such as a toothpick 53 may be removably sheathed. Sheath 51 is open ended on both ends, thus providing for effective drying out of humidity.

As known in the art, longitudinal grip portion 5 may comprise a battery powered electric motor 55, a battery 57 and links 55 and 61 to impart vibrating motion or rotational motion of the tufts of of bristle bundles 19, as is well known in the art. Vibrating motion and rotational motion may be similarly imparted to the turfs of bristle bundle 21.

It will be appreciated by those skilled in the art that the invention is not limited to what has been shown and described hereinabove by way of example only. Rather, the invention is limited solely by the claims which follow.

What is claimed is:

1. A toothbrush having at least one brushing head disposed at one of its ends, the toothbrush comprising a handle, the handle comprising a longitudinal grip portion and at least one bifurcated end portion, the bifurcated end portion comprises two cleansing means carrying members each having a flexible neck portion, said carrying members constructed to allow resiliently variable distance therebetween, and sufficiently spaced to allow mounting cleansing means thereon, cleansing means comprising a pair of brushing heads formed of bristle bundles arranged at the extremities of said carrying members, wherein the free ends of said bristle bundles of each of said brushing heads define a plane substantially perpendicular to the direction of the bristle, and wherein said bristle bundles are inclined to one another at an angle ranging between 60° and 120, so that said brushing heads are inclined to one another substantially at said angle.

2. A toothbrush as in claim 1, wherein said brushing heads having each a free end, and wherein said free ends converge at an angle, or are proximate to such convergence.

3. A toothbrush as in claim 1, wherein said angle is about 90°.

4. A toothbrush as in claim 1, wherein said brushing heads are removably connected to said carrying members allowing removal and discarding of said brushing heads.

5. A toothbrush as in claim 1, further comprising a lateral sheath in which the handle of an oral hygiene implement is removably sheathed.

6. A toothbrush as in claim 1, wherein said longitudinal grip portion comprises a battery powered electric motor to impart vibrating motion.

7. A toothbrush as in claim 1, wherein said longitudinal grip portion comprises a battery powered electric motor to impart motion of tufts of said bristle bundles.

8. A toothbrush having at least one brushing head disposed at one of its ends, the toothbrush comprising a handle, the handle comprising a longitudinal grip portion and at least one bifurcated end portion, the bifurcated end portion having two cleansing means carrying members comprising flexible neck portions extending in parallel directions, constructed to allow resiliently variable distance therebetween, said carrying members being sufficiently spaced so as to allow mounting cleansing means thereon, said carrying members comprise two types of spaced apart cleansing means so that a first type of said cleansing means is disposed at the upper extremities of said carrying members and a second type of said cleansing means is disposed at the lower extremities of said carrying members, respectively, each of said cleansing means comprising at least one of the following: (i) a pair of brushing heads comprising bristle bundles arranged at the extremities of said carrying members; (ii) a dental floss tautly stretched across said carrying members.

9. A toothbrush as in claim 8, wherein said pair of brushing heads being angled in respect to one another, said pair of brushing heads being connected to said handle by means of said flexible neck portions, and wherein the free ends of said brushing head converge at an angle, or are proximate to such convergence.

10. A toothbrush as in claim 9, wherein the angle between said brushing heads ranges between 120° and 60°.

11. A toothbrush as in claim 10, wherein said angle is about 90°.

12. A toothbrush as in claim 8, wherein said pair of brushing heads comprises two oppositely facing small brushing heads holding bristle arrangements for simultaneously brushing both sides of a tooth.

13. A toothbrush as in claim 12, wherein said oppositely facing small brushing heads being spaced apart, so that the space therebetween substantially matches the typical width of a tooth.

14. A toothbrush as in claim 12, wherein said small brushing heads are inclined to one another at a predetermined angle.

15. A toothbrush as in claim 14, wherein said predetermined angle ranges between 60° and 120°.

16. A toothbrush as in claim 15, wherein said predetermined angle is about 90°.

17. A toothbrush as in claim 12, wherein said small brushing heads are removably connected to said carrying members to allow removal and discarding of said small brushing heads.

18. A toothbrush as in claim 8, wherein said longitudinal grip portion comprises a protrusion mounted thereon, about which said dental floss may be wrapped and secured, and said carrying members comprise at their tips large openings through which said floss may be passed and tautly stretched.

19. A toothbrush as in claim 8, wherein said cleansing means carrying members comprise each a head portion connected to said handle by a neck portion, said head portions comprise a leg curving downward from said neck portion, one type of said cleansing means is disposed at the lower extremities of said legs and another type of said cleansing means is disposed at the area of connection between said neck portions and said head portion, respectively.

20. A toothbrush as in claim 8, wherein said first type of cleansing means comprises a disposable dental floss tautly stretched across said carrying members, and said second type of cleansing means comprises two oppositely facing small brushing heads holding bristle arrangements for simultaneously brushing both sides of a tooth, said oppositely facing small brushing heads being spaced apart so the space there between substantially matches the typical width of a tooth.

21. A toothbrush as in claim 8, further comprising a lateral sheath in which the handle of an oral hygiene implement is removably sheathed.

22. A toothbrush as in claim 8, wherein said longitudinal grip portion comprises a battery powered electric motor to impart vibrating motion.

23. A toothbrush as in claim 8, wherein said longitudinal grip portion comprises a battery powered electric motor to impart motion of tufts of said bristle bundles.

24. A toothbrush comprising a handle having a longitudinal grip portion, a first and a second bifurcated end portions disposed at longitudinally opposite sides of said grip portion, each comprising two cleansing means carrying members sufficiently spaced to allow mounting cleansing means thereon, a first of cleansing means comprising a pair of mutually inclined first brushing heads formed of bristle bundles arranged at the extremities of said carrying members of said first bifurcated end portion; and, wherein said carrying members of said second bifurcated end portion, being constructed to allow resiliently variable distance therebetween, each having a flexible neck portion, and wherein said cleansing means is selected from a list consisting of:
   a) two oppositely facing small brushing heads holding bristle arrangements for simultaneously brushing both sides of a tooth; and,
   b) a dental floss tautly stretched across openings disposed at the tips of said carrying members, said floss being wrapped and securable about a protrusion mounted on said longitudinal grip portion.

25. A toothbrush as in claim 24, wherein said oppositely facing small brushing heads being spaced apart, so the space therebetween substantially matches the typical width of a tooth.

26. A toothbrush as in claim 24, wherein said small brushing heads are inclined to one another at a predetermined angle.

27. A toothbrush as in claim 26, wherein said predetermined angle ranges between 160° and 180°.

28. A toothbrush as in claim 27, wherein said predetermined angle is about 170°.

29. A toothbrush as in claim 24, wherein each of said carrying members having an upper and a lower extremity distal from said grip, and wherein said small brushing heads are arranged at opposing said lower extremities, and wherein said openings are disposed at said upper extremities respectively.

30. A toothbrush as in claim 24, wherein said first brushing heads, or said small brushing heads are removably connected to said carrying members, allowing removal and discarding thereof.

31. A toothbrush as in claim 24 further comprising a lateral sheath in which the handle of a toothpick is removably sheathed.

32. A toothbrush as in claim 24, wherein said longitudinal grip portion comprises a battery powered electric motor to impart vibrating motion.

33. A toothbrush as in claim 24, wherein said longitudinal grip portion comprises a battery powered electric motor to impart motion of tufts to at least one of said bristle bundles.

34. A toothbrush having at least one brushing head disposed at one of its ends, the toothbrush comprising a handle, the handle comprising a longitudinal grip portion and at least one bifurcated end portion, the bifurcated end portion having two cleansing means carrying members comprising flexible neck portions extending in parallel directions, said carrying members being constructed to allow resiliently variable distance therebetween, and being sufficiently spaced so as to allow mounting cleansing means thereon, said cleansing means comprising at least one of the following: (i) a pair of brushing heads comprising bristle bundles arranged at the extremities of said carrying members; (ii) a dental floss tautly stretched across said carrying members, and spaced apart from said extremities, and said longitudinal grip portion comprises a battery powered electric motor to impart vibrating motion.

35. A toothbrush having at least one brushing head disposed at one of its ends, the toothbrush comprising a handle, the handle comprising a longitudinal grip portion and at least one bifurcated end portion, the bifurcated end portion having two cleansing means carrying members comprising flexible neck portions extending in parallel directions, constructed to allow resiliently variable distance therebetween, said carrying members being sufficiently spaced so as to allow mounting cleansing means thereon, said cleansing means comprising at least one of the following: (i) a pair of brushing heads comprising bristle bundles arranged at the extremities of said carrying members; (ii) a dental floss stretched across said carrying members and spaced apart from said extremities, and said longitudinal grip portion comprises a battery powered electric motor to impart motion of tufts of said bristle bundles.

36. A toothbrush comprising a lateral sheath fixedly attached thereto and having two open ended sides, in which the handle of toothpick is removably sheathed.

* * * * *

UNITED STATES PATENT AND TRADEMARK OFFICE
CERTIFICATE OF CORRECTION

PATENT NO : 6,138,689
DATED : Oct. 31, 2000
INVENTOR(S) : Stern

It is certified that error appears in the above-identified patent and that said Letters Patent is hereby corrected as shown below:

In the first page, Inventor Details [76] delete "Tel Aviv" and replace with --Bat Yam-- so that inventor address reads:
   Mina Miri Stern, 6 Uziel St., Bat Yam, Israel, 59463.

In col. 5 line 57, replace "55" with --59--.

In col. 5, line 58, delete third occurrence of the word "of"

Signed and Sealed this

Eighth Day of May, 2001

Attest:

NICHOLAS P. GODICI

Attesting Officer

Acting Director of the United States Patent and Trademark Office